United States Patent
Reed et al.

(10) Patent No.: US 6,524,239 B1
(45) Date of Patent: Feb. 25, 2003

(54) APPARATUS FOR NON-INSTRUSIVELY MEASURING HEALTH PARAMETERS OF A SUBJECT AND METHOD OF USE THEREOF

(75) Inventors: William C. Reed, Portland, OR (US); Lydia Lundberg, Portland, OR (US); Frank M. Bouton, Beaverton, OR (US); William Pascoe, Rainier, OR (US); Robert Ornstein, Portland, OR (US)

(73) Assignee: WCR Company, Portland, OR (US)

( * ) Notice: Subject to any disclaimer, the term of this patent is extended or adjusted under 35 U.S.C. 154(b) by 0 days.

(21) Appl. No.: 09/706,327

(22) Filed: Nov. 3, 2000

Related U.S. Application Data
(60) Provisional application No. 60/163,709, filed on Nov. 5, 1999.

(51) Int. Cl.[7] .............................. A61B 5/00; G06F 11/00; G06F 15/00; G06F 17/60
(52) U.S. Cl. .................. 600/300; 702/188; 128/920; 705/2
(58) Field of Search ................................ 600/300–301, 600/481–486, 500–508, 529–538, 544–545, 587–595; 705/2–3; 128/903, 904, 920–925; 702/188

(56) References Cited

U.S. PATENT DOCUMENTS

| | | | | |
|---|---|---|---|---|
| 5,343,869 A | * | 9/1994 | Pross et al. ................. | 600/301 |
| 5,410,471 A | * | 4/1995 | Alyfuku et al. ............. | 600/300 |
| 5,780,798 A | * | 7/1998 | Hall-Jackson ............. | 200/85 R |
| 5,950,632 A | * | 9/1999 | Reber et al. ................. | 128/898 |
| 6,050,940 A | * | 4/2000 | Braun et al. ................. | 600/300 |
| 6,073,046 A | * | 6/2000 | Patel et al. .................. | 600/509 |
| 6,113,539 A | * | 9/2000 | Ridenour ..................... | 600/300 |
| 6,290,646 B1 | * | 9/2001 | Cosentino et al. .......... | 600/300 |
| 6,302,844 B1 | * | 10/2001 | Walker et al. .............. | 600/300 |

* cited by examiner

*Primary Examiner*—Max F. Hindenburg
*Assistant Examiner*—Michael Astorino
(74) *Attorney, Agent, or Firm*—Marger Johnson & McCollom, PC

(57) ABSTRACT

An integrated subject monitoring system facilitates measurement, collection and analysis of data pertaining to the health status of a subject. The system includes a network-coupled computer and subsystems monitoring subject location within a defined space and the curtilage thereof and obtaining measurements of a subject's physiological or behavioral/cognitive parameters within the defined space. Parameter data is obtained primarily passively, without the cooperation or active participation of the subject. A method of monitoring the physiological and behavioral/cognitive health status of an ambulatory subject involves monitoring in a primarily passive fashion, irrespective of the active collaboration of the subject. Subject health indicia parameters are continuously monitored, sampled and recorded. Captured values are compared to initial baseline values established for each of the measured parameters as well as to the trend for the parameter of that subject. Readings falling outside the boundaries trigger a signal to be sent to an appropriate party.

23 Claims, 3 Drawing Sheets

APPARATUS FOR NON-INSTRUSIVELY MEASURING HEALTH PARAMETERS OF A SUBJECT AND METHOD OF USE THEREOF

CLAIM OF PRIORITY

This application claims priority from U.S. Ser. No. 60/163,709, entitled CREATING AN AUTONOMY-RISK EQUILIBRIUM TECHNOLOGY, filed Nov. 5, 1999 and incorporated by reference herein.

BACKGROUND OF THE INVENTION

The present invention relates generally to health monitoring apparatuses, and more specifically to a system for non-intrusively monitoring the health status of a subject.

A subject's health status is typically evaluated by reference to a plurality of vital signs, such as pulse and respiration rates, temperature, blood oxygen saturation, weight and body hydration. Additional considerations include observations as to subject appearance and movement. These latter factors are also indicative of the subject's mental health, e.g., cognitive ability. Other cues are the degree of animation, compliance with responsibilities such as self-medication, forgetfulness as to whereabouts or activities, and the like.

In traditional residential care facilities, these indices are measured and observed by caregivers. While measurements are generally recorded, a portion of the observations is retained only in the institution's memory. This fact is especially true in the case of cognitive health cues.

Retention of caregiving personnel serves the critical role of logically preserving of the meaning and functionality of health data. Interacting with a patient over a period of time, a caregiver learns a great deal about the habits and individual vital sign trends of that patient. The large volumes of observed data provide evidence to support the diagnostic requirements of residential care professionals. Raw data pertaining to a subject's health status functions to provide the context in which present parameter values can be assessed.

With caregiver turnover, this context is minimized or lost unless the observed information has been reduced to writing for the new personnel. Typically, a fraction of the total observed data is so recorded. Sub-clinical observations are frequently useful in assessing subject health status, especially cognitive abilities. These data include subject demeanor, alertness, regularity and subject mobility. The common denominator is that these characteristics change gradually. They are therefore less noticeable to new personnel, who have not observed the subject over time and are not familiar with these characteristics.

Short institutional memory produces a lengthening of the time before caregivers or other health professionals become cognizant of a slow decline in a subject's health status. The delay in appreciating a decline causes a corresponding delay in responding to health deterioration of the subject. As a result, the subject suffers a depression in the quality of health care received.

SUMMARY OF THE INVENTION

One aspect of the present invention is an integrated subject monitoring system. The system facilitates measurement, collection and analysis of objective and subjective data pertaining to the physiological and behavioral health status of a subject.

The system includes a network with a computer, data storage device and data analysis means. Raw data and analyses can thereby be accessed by the subject or resident caregiver. Additionally, this information can be remotely accessed by a health care provider, family member or other authorized entity.

Further included are subsystems, operative to obtain measurements of a subject's physiological or behavioral/cognitive parameters within a defined multi-room space. Parameter data is measured primarily passively and without the intentional cooperation of the subject. According to this aspect of the present invention, the majority of the health parameter data can be obtained without relying upon the subject to remember or to actively participate in data acquisition.

The system of the present invention provides for prompts to be given a subject, to promote activities such as medication compliance, continence, and interactive parameter measurement. These prompts serve both to increase compliance as well as to encourage and reinforce routine behaviors and activities.

Additionally, the system comprises a subsystem to monitor subject location within the defined space and the curtilage thereof. This monitoring is performed without direct human supervision. Upon the request of a user, the system provides real-time information concerning the location of a monitored subject. Analyzed as a function of time, positional measurements provide locomotive information about the subject.

Further, control of ambient/environmental conditions is effected through the system of the present invention. Environmental inputs by a subject are recorded, enabling a system user to assess physical as well as cognitive aspects of the subject.

Another aspect of the present invention is a method of monitoring the physiological and behavioral/cognitive health status of an ambulatory subject, wherein the monitoring is primarily accomplished passively and without the active cooperation of the subject.

Indicia of physical and mental health are monitored by the system. An initial baseline is established for each of the measured parameters. Subject parameters are continuously sampled and recorded. Each reading is compared to the baseline as well as to the trend for the parameter of that subject. A user inputs parameter boundaries, which then serve as predetermined thresholds for that parameter. When a reading falls outside the boundaries, the system triggers a signal to be sent to an appropriate party.

Using chronological identifiers, the system can also determine physical or behavioral anomalies as a function of time. A user can set the system to transmit an alert when two or more parameter deviations occur contemporaneously. Thus, the system can be instructed that a combination of discrete deviations is of sufficient concern that warning message is merited, even when any one of the deviations could not trigger a warning.

DETAILED DESCRIPTION

As used herein, certain terms are meant to convey specific meanings. In the taking of a measurement by a sensor, "passive" or "irrespective of subject cooperation" means that the parameter measurement occurs without conscious collaboration on the part of the subject to accomplish a measurement. Lack of cooperation means that, for those health parameters measured passively, the subject need not even be aware that a sensor is present or that a measurement is being taken.

The term "ambulatory" means that the subject is capable of perambulation without personal assistance; i.e., the subject is not bedridden.

A cognitive parameter is a parameter indicative of the mental process or faculty of a subject, including abilities such as awareness, perception, reasoning, memory and judgment. A behavioral parameter refers to an indication in the form of an action of a subject, as well as a reaction in response to an external or internal stimulus. As used hereinafter, the term "cognitive" encompasses both cognitive as well as behavioral cues.

Figure 1:
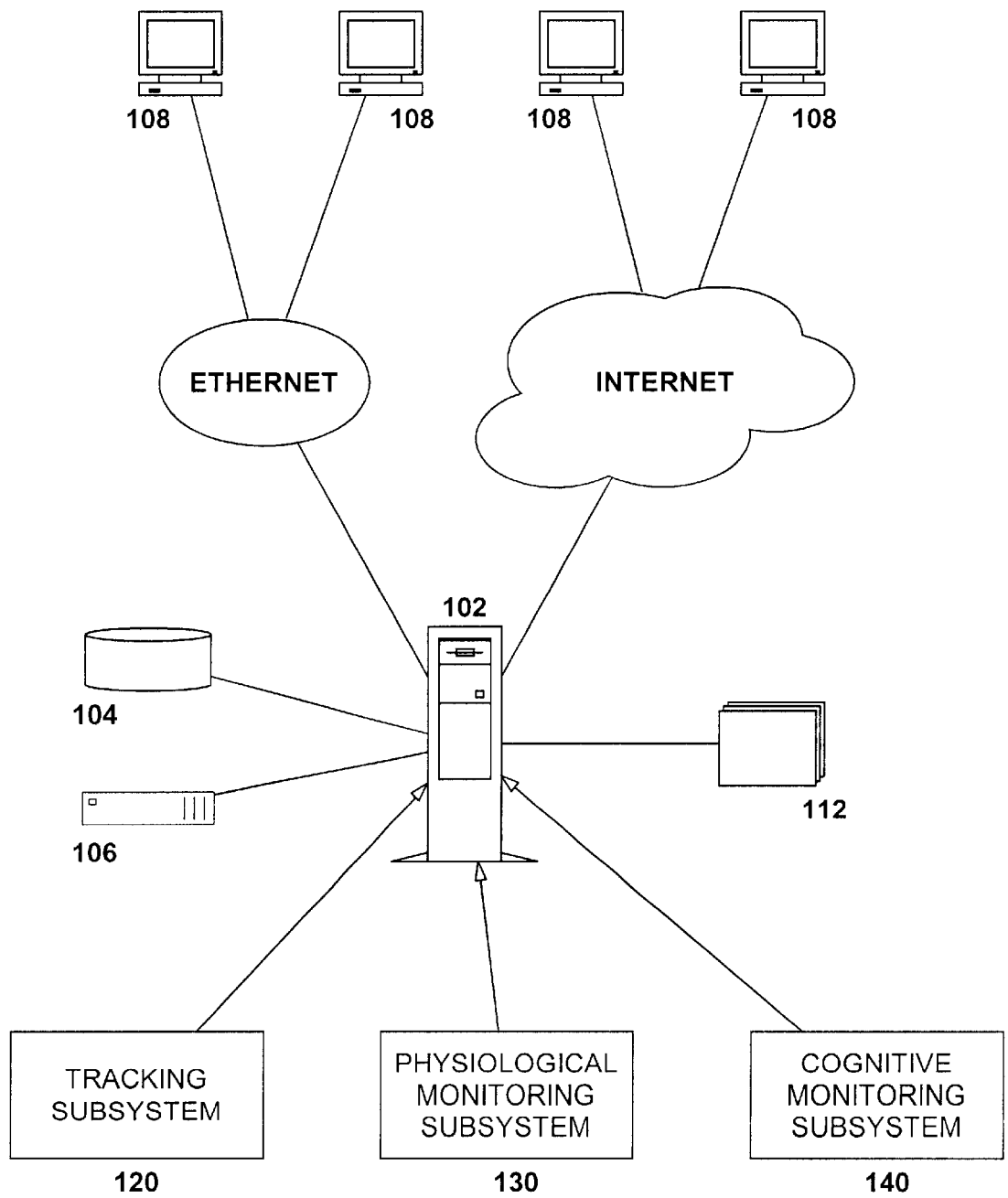
FIG. 1 is a block diagram of the system according to the present invention.

A first aspect, of the present invention is a health monitoring system, being operative to monitor physiological and behavioral/cognitive indices of a subject. As shown in FIG. 1, the system comprises a computer 102 coupled to a network, the network being accessible by at least one remote node 108. The computer is further coupled to a plurality of monitoring systems, described in detail infra.

The network comprises a computer 102 with a data storage device 104, wherein the collected measurement data resides. The computer is programmed to collect information in the form of measurements, associate subject identity codes (SIC) therewith, further associate chronological identifiers (i.e., a time stamp) where appropriate, and store the data record. Coupled to the computer, a data analysis means 106 is used to analyze the stored data records. The types of analyses are discussed in more detail, infra.

System outputs comprise health status and care reports 110 and billing summaries 112. These reports can be delivered via conventional methods or accessed via one of the remote nodes 108.

Caregivers are responsible for recording via a remote network node 108 the types of services provided to each subject. In traditional residential care settings, caregivers must hand-write notes. The system according to the present invention enables caregivers to log furnished services via a touch screen, palmtop digital assistant, keyboard, or other input device. This computerized process decreases the amount of time caregivers spend writing down notes and maximizes the time that can be devoted to the provision of care services.

As needed, a caregiver also inputs general observations pertaining to a subject. As well, a subject can enter comments and non-observable complaints and symptoms. These comments are entered into one of a plurality of terminals 108 distributed throughout the defined space. The terminals can also have voice recognition software or optical character recognition scanners so that caregivers can enter information without typing. A person skilled in the art will also recognize other ways information can be entered into the system.

As with other measurements, entered data is associated with a chronological identifier and stored. This data point can be used in caregiving assessments as well as summaries 112. Summaries can include billing statements, care reports and other matters, generated and distributed either online or through traditional avenues.

Subject location and movement, physiological, cognitive parameters are monitored by subsystems of the present invention. These subsystems gather data from which the health status of the subject can be determined. The data-gathering sensors report information to the system, which then identifies the measured subject using the tracking subsystem data. The system thereby can associate a subject identification code (SIC) and a chronological identifier to the parameter datum.

A first monitoring subsystem is a tracking subsystem 120, useful to monitor the location and mobility of a subject. Each subject carries a small radio frequency (RF), infrared (IR), or other wireless personal transmitter, transmitting a code unique to that subject. A subset of the sensors is RF-, IR-, or other wireless receivers, distributed throughout the defined space and its curtilage. As the subject moves about in this region, sensors detect subject presence and signal the system of the subject's location.

The personal transmitters act as identification badges and serve as keys to accessible rooms. Each personal transmitter further possesses a "panic button", enabling the subject to issue an emergency call to the system in the event immediate attention is required. So activated, the personal transmitter notifies the system of both the identity and exact location within the facility of the subject. This information shortens reaction time and permits a customized response.

By the association of chronological identifiers to these signals, the system can calculate locomotion data informative as to a subject's mobility, i.e., walking speed. Further, overall distance traveled can be assessed, both to evaluate the level of the subject's activity and exercise as well as to detect any decline in locomotive ability.

If a subject exceeds predetermined boundaries, such as entering an off-limits room, or walking beyond a certain radius from the facility, the system can page or otherwise alert an appropriate party, i.e., a caregiver. In such an instance, a caregiver can check a network terminal to learn the subject's exact location. A caregiver in one location can thereby respond instantaneously to any of a plurality of ambulatory subjects. The system maintains continuous monitoring as subjects move freely throughout the space. Subjects also feel a sense of freedom, moving about the area ad libitum and unaccompanied, without reducing personal safety.

Direct monitoring of a subject is accomplished by a physiological monitoring subsystem 130 and a cognitive monitoring subsystem 140. Each of these subsystems comprises at least one sensor coupled to the networked computer. Preferably, a plurality of sensors are distributed throughout the area in which the subject can move, such that the chronological gap between any two consecutive parameter samplings is minimized, regardless of the location of the subject within the area.

Input in the form of data signals is received from a plurality of sensors and from remote network nodes. Both the sensors and the remote nodes are distributed throughout the defined multi-room space. For each sensor, a coupled signal generator generates a digital signal corresponding to the obtained measurement. The signal is then transmitted to the networked computer, associated with a subject identification code, and then stored and analyzed.

The tracking subsystem makes possible the use of promiscuous sensors, which measure parameters without regard for the identity of the monitored subject. By reviewing subject identities and locations from the tracking subsystem, the system can determine the identity of the subject sufficiently proximate to the signaling sensor for measurement to be achieved. That subject's SIC is then associated with the parameter measurement signal from the sensor.

Figure 2:
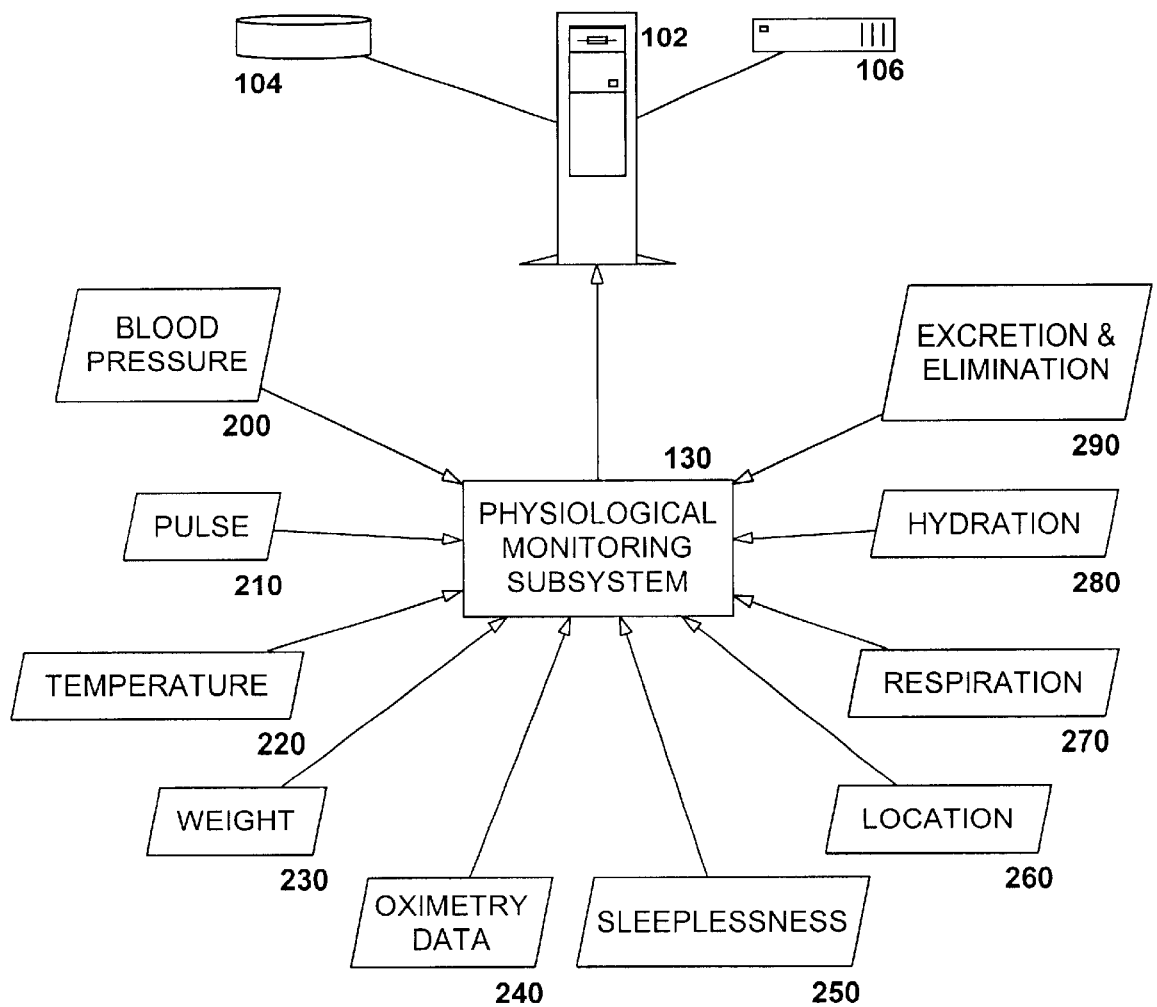
FIG. 2 is a block diagram of the physiological monitoring subsystem of the system of FIG. 1.

Turning now to FIG. 2, the physiological monitoring subsystem comprises sensors to measure vital signs and other health parameters of a subject. These parameters are preferably blood pressure 200, pulse 210, temperature 220, weight 230, oximetry data 240, sleeplessness 250, subject location 260, respiration rate 270, body hydration 280, and excretion/elimination data 290.

A subset of the plurality of sensors measures parameters with the active collaboration of the subject. These sensors comprise a cuff to measure blood pressure 200, an oximetry 240 device, a respiration 270 monitor and a remote node 108, preferably a computer terminal, at which the subject can enter subjective inputs. A person skilled in the art will also recognize other sensors which can measure parameters with the active consent of the subject. Collaborative sensors can be stationary devices; alternatively, a telemetric sensor can be worn by the subject and the data transmitted from it to a proximate receiver. Distribution of receivers throughout the defined space permits the subject to move therethrough with uninterrupted data acquisition and transmission by the system.

In contrast to the subset of sensors discussed, supra, a second subset of the system's sensors obtain parameter measurements irrespective of subject cooperation. More specifically, those sensors are operative to measure physiological or cognitive parameters as the subject engages in everyday activities generally unrelated to health monitoring. The sensors comprise many types, including thermocouples, infrared and motion sensors, conductive elements, force sensors and other transducing sensors. A person skilled in the art will also recognize other sensors that can be used.

As an example, a load sensor can be embedded in a chair in the subject's personal living space, enabling body weight 240 to be measured whenever the subject sits in the chair. In this manner, the subject need not use a conventional scale, consciously report the weight reading, or even be aware that the load sensor resides in the chair. The unrelated act of sitting in the chair, e.g., to rest, read or watch television, is sufficient to enable the system to obtain a body weight measurement.

Weight 230 is detected via force sensors positioned to measure z-axis force applications to the subject's sleeping surface. These sensors thus enable determination of the mass of an object or person resting on the surface. Sleeplessness 250 can be simultaneously measured using additional sensors to detect lateral motion of the surface owing to movement of the subject. Occurring during the night, this movement is indicative of subject restlessness and can be utilized to perceive and quantify sleep difficulties or disorders.

Examples of other sensor types and their deployment include a plurality of sensors embedded in a toilet seat in a subject's living space. During a routine toileting event, these sensors can measure temperature, pulse, hydration and weight.

Temperature 220 and body hydration 280 can be measured by thermocouples in the seat. A set of conductive elements, embedded in the toilet seat, measure body impedance during a routine toileting event. From this impedance data, both pulse and body hydration can be calculated. These calculations are well-known in the art.

Bowel movement and urination 290 are monitored by sensors in the toilet seat and bowl. Thermocouples in the seat and bowl measure the subject temperature 220 and the temperature of the bowl contents, respectively. As well, force sensors provide weight 230 readings at the beginning and end of the toileting event. Changes, occurring during the toileting event, in subject weight and in the temperature of the bowl contents can be used to calculate the fecal mass and/or urine volume of the event. The data also displays the subject's regularity in terms of frequency and volume. When accumulated over time, this information is useful to detect changes in the subject's habits or abilities. These changes can be due to physical problems or to declining mental faculties.

Similarly, force sensors, e.g., load cells, are employed elsewhere to detect the subject's weight 230. Force sensors are deployed under the legs of the subject's bed, in the feet or casters of a chair in the subject's living space, or in a toilet seat/footpad arrangement. Body mass is appreciated when the subject rests on the article in which the force sensors have been inserted.

Temperature 220 is also monitored with a thermal (infrared) camera, which scans a part of the subject's body such as the forehead. This scan can occur while the subject is engaging in any routine activity, i.e., applying makeup in front of a mirror, using a computer terminal, or other activity in which the subject's head is predicted to be within the defined zone of sensor measurement. From this scan, the system determines the relative body temperature without physically contacting the subject or interfering with the subject's normal activities.

Figure 3:
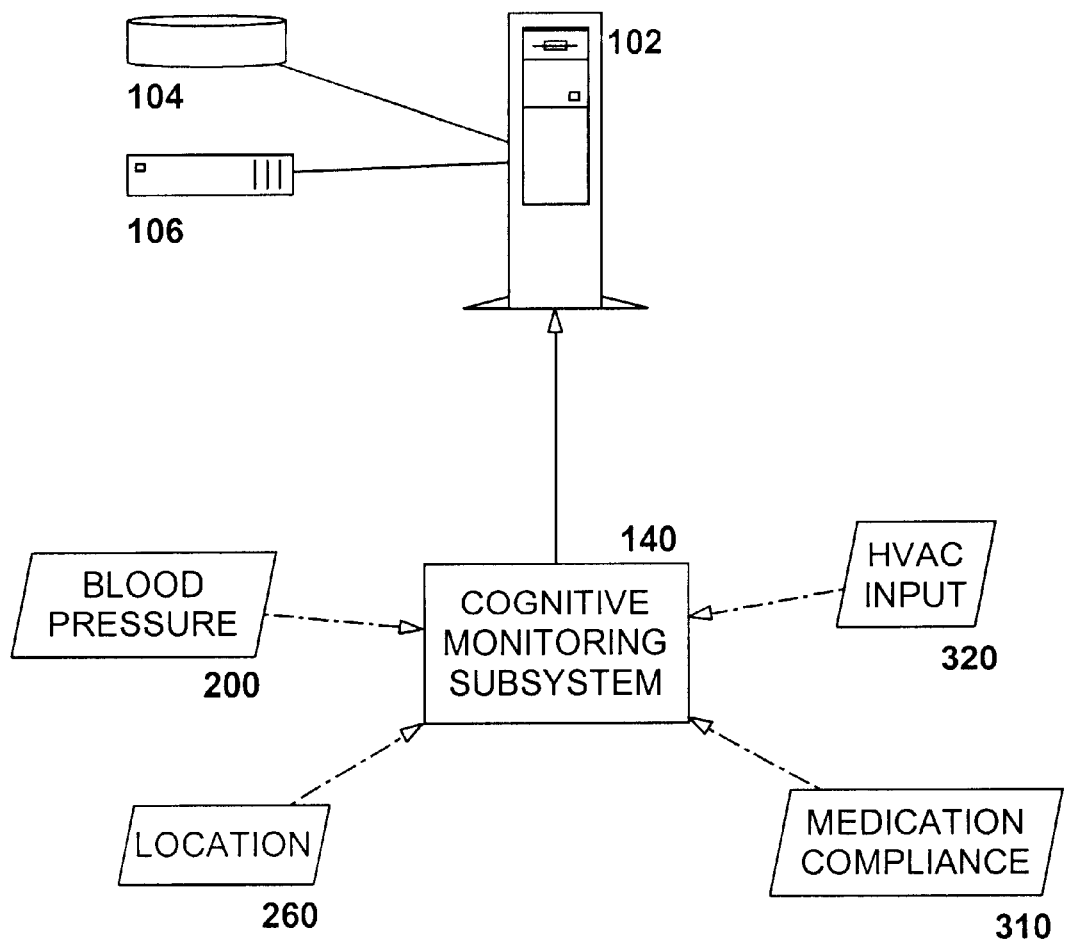
FIG. 3 is a block diagram of the cognitive monitoring subsystem of the system of FIG. 1.

The system according to the present invention further comprises a cognitive monitoring subsystem 140, measuring indices of the mental health of a subject. This health is specifically focused on the awareness, perception, reasoning, memory and judgment of the subject. The cognitive monitoring subsystem is show in FIG. 3.

These parameters are also measured primarily passively and without subject cooperation. Some of the indicia are derived from interactive behavior otherwise unrelated to the measuring of a cognitive parameter.

An example of the direct measurement of a cognitive parameter is observation of medication compliance 310. Data is generated from a medication compliance device, provided to each self-medicating subject. The device includes a sensor to record opening and closing of the medicine cabinet door. Load cells are positioned beneath each medicine container and are operative to record the mass of a container and its contents. By controlling the size or shape of the containers, each container can be uniquely and consistently identified. The load cells are sufficiently discriminating to discern when a pill or tablet has been removed from a container, indicating that the patient has removed medication corresponding to that container.

An incremental decline in medication compliance can be illustrative of declining mental faculties. By recording compliance over a significant period of time, this slow deterioration in compliance can be noted by a caregiver or other health professional.

Indirectly, cognitive indicia are obtained by evaluating irregularities in subject behavior. Sudden changes in adjustment of environmental controls or lighting 320 can also signify aberrant behavior. Failure to submit to routine, interactive parameter measurements, such as blood pressure 200, are detected from the data generated by the physiological monitoring subsystem 130. Variations in restroom By the same token, eccentric movement, wandering and improper attempts to enter personal living spaces of another subject are indicative of forgetfulness and confusion. The system can analyze mobility data 260 to determine instances wherein the subject mistakenly tried to enter another subject's room, wandered or repeatedly visited the toilet when not necessary. By tracking mobility over time, a health professional can assess discrete wanderings in the context of the subject's normal routine, as established over a period of time. Declines in cognitive ability are thereby more readily appreciated.

The subject is empowered to disable data acquisition relating to one or more parameters, by deactivation of either a sensor in the subject's personal living space or of the subject's unique transmitter. In the latter instance, the system is not stopped from acquiring the measurement; the system is simply unable to associate a subject identification code with the value.

Deactivation by a subject of data collection for that subject can be inadvertent. Conversely, the subject can feel the need for greater personal privacy, whether generally or to engage in an activity having the potential to trigger an alert. While the subject is free to disable data collection, the deactivation event itself is duly recorded. Such events are noteworthy, as they can indicate a change in mental health status or an intentional obstruction of proper system operation.

Redundancy is employed to maintain a continuous stream of data, even in the face of changes in the subject's daily routine. Using body temperature as an example, thermocouples are embedded in the subject's toilet seat as described. The thermal camera acquires temperature data in a different location. Thermocouples are also embedded in other everyday objects in still other locations. Because sensors are embedded within everyday objects, the sensor cannot obtain measurements when the article in which it is embedded breaks or is otherwise out of service. By using a plurality of sensors to measure a single parameter, that parameter can be constantly monitored even if, for example, a specific wall-mounted sensor fails or the subject's toilet becomes temporarily unusable.

The passive acquisition of physiological and behavioral measurements ensures greater compliance with data measurement and recordation than occurs in traditional residential care procedures. Long-term record-keeping permits a current measurement to be viewed in the context of the patient's individual history for the given parameter. This "institutional memory" improves evaluation of the subject's health status.

Deviations from the subject's normal values are also more rapidly brought to the attention of an appropriate party, e.g., health care provider, on-site caregiver, subject or other entity authorized to access the data. Lastly, the subject's daily activity and routine are impacted much less than in traditional residential care facilities, where a patient must submit to a caregiver's measuring of parameters, i.e., temperature or pulse.

The sensors are coupled to the network via wired or wireless connection. Data transmission of signals to the data storage device is thereby enabled without regard for the type of sensor or coupling means for that particular sensor.

The system uses a variety of audible and visual cues to prompt subject behavior and compliance. For example, a simple chime or other tone can be employed to signal meals. As a more relevant example to health and elder care, a colored or flashing light in the subject's medicine cabinet can be used to signal medication intake. A tone, synthesized voice or email message can be employed to signal the need for a parameter to be interactively measured. The system can turn on the subject's room lights during the night to wake the subject and prompt a toilet visit to maintain continence. A tone can also be used both to signal when a subject nears the limits of the monitored area and as a more general warning that the subject is about to leave the facility grounds. As is well-known with wireless paging technology, a vibration or silent mode alert can be employed to provide the subject a greater level of privacy. A person skilled in the art will also recognize other cues that can be used.

Output of the system according to the present invention comprises summaries and request responses for each monitored subject. The outputs are tailored for each receiving party (e.g., subject, physician, caregiver, or subject's family member). Reports provide detail on subject health over each reporting period. Data in these reports includes provided care services, described by frequency, type, and cost; types of activities in which the subject participated (again, by frequency and type); and a movement report. These summaries provide specific health information and also convey a more general representation of the subject's quality of life and care in the facility. Caregivers and administrative personnel are relieved of the task of relating this information to physicians, family members, and others. Thus freed from performing a number of administrative duties, caregivers can devote a greater portion of their time to the provision of services and care of the subjects.

Remote access to data by off-premises persons facilitates the sharing of subjective and objective measurements, and transmits information in a user-friendly format through digital channels. Access by health professional, family members and other off-premises persons is through a network connection. The subject controls access and the degree of viewable information for each party desiring to view subject data. Subject data privacy is thereby assured with respect to each type of viewer, i.e., physician, family member or other person permitted to view such information.

It should be apparent that the system of the present invention can be applied to subjects of various states of health. The system is most efficacious when applied to fully ambulatory subjects but can be adapted to monitor subjects requiring ambulatory assistance.

Another aspect of the present invention is a method of monitoring indicia of the health status of a subject. Monitoring is performed in a predominantly passive manner, without the cooperation of the monitored subject.

In residential care facilities, deviations from the standard parameter values are significant and receive the attention of a caregiver or health care provider. As discussed, caregiver turnover reduces the familiarity of any one caregiver with the broad history of a particular patient. The system of the present invention improves patient care by serving as the "institution", compiling and retaining a detailed history of all of the pertinent health parameter measurements of a subject.

A corollary feature of this role is to sooner detect large or frequent changes in data patterns. By compiling a large body of information describing a subject's health history in terms of certain parameters, the system readily detects variations in data patterns as they occur. The system can thereby immediately alert the proper party of the deviation. To accomplish this goal, data is logged and analyzed for comparison with against pre-established limits. When the parameter measurement falls outside the pre-approved range of values, a notification is issued to the appropriate party for remedial action.

Prior to and during move-in to the facility, subjects complete different profiles, summarizing financial, health, system, and personal information. These assessments are stored by the system.

The health assessment will be the basis for a health care service plan. The system profile establishes health parameters and negotiated risk agreements, described in greater detail below. The personal assessment is a list of several hundred questions that subjects complete to help staff quickly find commonalities with other subjects and staff, these persons having also completed the profile assessment. The profiles are maintained in a database in the system's data storage device, such that they can be queried by caregivers, administrators and other authorized parties.

The present invention permits the establishment of dynamic parameters in three categories of subject health: vital signs, inputs/outputs, and behavior and cognitive indices. These parameters are individualized and explicit. They are formalized in a negotiated-risk agreement executed by the elderly subject, physician, family, and caregiver. Negotiation by these parties of parameters give subjects levels of independence and risk-taking ability that neither affect facility liability exposure nor jeopardize the personal safety of the subject. The parameters can be amended from time to time, according to changes in a subject's cognitive and/or physical capabilities.

This negotiation also determines whom to notify when any one of a number of events occurs. One such event is a subject parameter exceeding the predetermined threshold. Alternatively, a number or particular group of parameters can be out of compliance before an alert is warranted. In another example prompting an alert, a subject parameter can show a large percentage change from one measurement to the next. By tracking movement in parallel with other parameters, the system can discern when a pulse or temperature increase is due to heightened activity rather than the result of a health aberration.

The method comprises providing a networked monitoring system, as described above. Generally, a plurality of detectors are positioned within the defined space, each of the plurality of detectors capable of detecting a physiological parameter of the subject. Examples of physiological parameters have been previously described and include, for example, pulse 210 or weight 230.

Parameter values are then passively measured, without subject cooperation or active participation in the measurement step. A signal corresponding to the measured parameter value is generated and transmitted to the data storage device. The measured parameter value is associated with a subject identifier and, where applicable, a chronological identifier.

In taking these initial parameter measurements, the system thereby establishes a baseline value for each health component. Taken in tandem with the parameter limits established at the outset, the baseline constitutes the standard against which the system evaluates subsequent measurements.

Subsequent parameter trending establishes an ongoing history of the subject's physical and mental health, as well as providing a context in which to evaluate current measurements. Specifically, normal trends can be identified for each subject and parameter. In this way, normal fluctuations are more readily recognized and distinguished from abnormalities requiring health care attention.

This institutional memory provides a fuller record of objective and subjective observations regarding the subject. Against this tapestry, subtle deviations in vital signs, daily routine and cognitive performance are more accurately assessed and more promptly detected.

Occurrences calling for party signaling include instantaneous conduct-oriented events such as "panic" or emergency calls by subject or facility staff, disabling of one or more sensors by a subject, or deviations in one or more monitored health parameters.

Variations in parameter values are noted as they occur, with alerts generated according to response criteria defined by a system operator. The system permits the assignment of priorities to the various parameters, as well as to the degree of deviation necessary before an alert will be generated and sent.

For less critical parameters, variations are merely noted. On the other hand, detection of a medically significant parameter aberration can be set to prompt an immediate notification event. Upon receiving an emergency call from a subject's personal transmitter-signifying that immediate attention is required-the system responds with appropriate cues to garner the attention of the proper party, including light, sound and pager signals.

The patient monitoring and tracking system and method of the present invention use real-time data collection and digital communication to improve the health care and quality of life of subjects in assisted living facilities, residential care facilities, adult foster care homes, and private residences serviced by community-based care.

The present invention is uniquely adapted to these care settings. It develops, adapts, and integrates thermal infrared monitoring, sonic recognition, radio frequency transmitters and other technologies. These technologies are combined with Internet-based communication networks to monitor human health and provide behavioral cues to prolong subject independence. The monitoring system according to the present invention gathers, logs, and transmits health-related data such as body temperature, oximetry, pulse, weight, hydration, blood pressure and mobility, doing so without interfering with subjects' normal activities or home environment. Ambient sensors control the heating, ventilation and air conditioning (HVAC) to suit subject needs.

The present invention differs from the traditional model of long-term care by reducing the amount of risk faced by facilities, thereby freeing them to fully experiment with and realize the potential of a subject-centered care model. In effect, the present invention shifts the paradigm of care back several generations, recalling a time when family members, country doctors, and others were closely in tune with an elderly person's history, condition, habits and preferences.

FEATURES AND BENEFITS

The system addresses the needs of at least five groups: subjects receiving health care; caregivers and care-giving facilities; the subject's families; physicians; and researchers. These groups presently do without important, reliably-gathered health information in most non-institutional settings. As a result, personnel caring for an elderly person living alone or in a large facility are often unable to proactively diagnose and treat illnesses.

Moreover, conventional scenarios frequently limit the time and attention given to any one subject. As well, staffing patterns in these settings-and the nature of operation of such institutions-often limit a resident subject's autonomy. Home health aides must visit several patients each day, restricting the amount of time devoted to data acquisition at any one site. Residential facility caregivers cannot monitor a large plurality of subjects simultaneously.

The system automatically records important physical and mental health indicators. Caregivers, freed from paperwork needed to meet accounting, insurance, and legal requirements, can spend more time with subjects. Health care personnel also gain a better understanding of subject health trends and can engage in meaningful conversations about the type of care provided. Staff can manually enter observations and other comments about a subject's daily life into the computer via touch screens and other technology found throughout the facility.

Logistic concerns and legibility issues are thereby reduced. Automated records also simplify billing and minimize problems associated with high caregiver turnover rates. Administrative practices are thereby substantially automated. As well, the care facility can receive subject feedback regarding quality of services, caregiving and physical resources. Subject comments, entered into the system, can be employed to improve the quality and efficiency of the facility.

In an elder care setting, the present invention grants subjects more control over their daily decisions without sacrificing their safety. Subjects have freedom to take risks which otherwise would be prohibited. Historical data recorded by the system gives subjects the ability to make informed choices about the type of care they receive. Dynamic risk-autonomy health parameters and custom health summaries give subjects incentives to improve their mental and physical well-being, thereby prolonging life and reducing health care costs. Prompts prolong subject independence as cognitive ability changes.

For the families of monitored subjects, family members can be informed as to the specific types, quantity and subject-perceived quality of health care services provided to the subject. Families receiving health summaries and billing breakdowns based on the information collected by the computer. Families need not rely solely on generic billing statements and the written notes of caregivers. The billing statements can include subject comments concerning quality of health care services, caregivers and the facility's physical resources, informing families thereon in substantially real-time. In addition, family members can be advised automatically of emergencies via real-time system-initiated data transfer over the Internet, via telephone or pager.

Doctors and other authorized persons needing detailed records on subject health have immediate access to necessary data via e-mail and the Internet. Trends for subject vital signs; system inputs and outputs; subject movement; frequency, variety and duration of activities; and other crucial information are accessed easily through the system computer. Physicians do not have to rely on written logs that are often maintained at the facility and frequently difficult to interpret. With a clearer understanding of health trends, physicians and others can prescribe treatment plans based on historical data. Computer-based alerts and records also speed response time.

Using system-recorded data, researchers can quantitatively judge the success of experimental intervention strategies that have been implemented at the subject's facility. As well, governmental agencies can measure quality of care in regulated facilities. The spatial monitoring component of the system can be especially useful for research addressing the influence of facility design on behavior.

As an example and not by way of limitation, an electronic scale having an embedded transmitter can be provided in a subject's living space. When the subject stands upon the scale, the measurement is transmitted by the scale to the networked computer for chronological identifier association. The scale can be hard-wired to the network or its location in the room can be fixed.

The system receives data from the spatial monitoring apparatus to indicate that Subject A is located in the rest room of Subject A's personal living space. Combining these data into a data record, the system can thereby determine that the scale sensors are weighing Subject A. This determination can be accurately made even if another monitored subject is contemporaneously present in Subject A's living space. By triangulating data received from the unique personal transmitter devices of the spatial monitoring apparatus, the system can discern that Subject A is located in the area of the room where the scale is also located.

Minor variations in subject parameters can be set to be recorded but not trigger alerts. For example, day-to-day fluctuations in body weight are normal, due to water retention, variations in meal size or heavier attire. If weight continues to fluctuate or continues in a relatively steady trend, an alert can then be transmitted to a health professional that the subject is gaining or losing weight, as the case may be.

In contrast, an elevation in a subject's body temperature is a less normal occurrence and is generally significant enough to warrant caregiver notification or attention. As described, the system can discriminate between health-related parameter departures and normal deviations flowing from everyday activities, such as exercise or other strenuous physical activity.

Similarly, detection of an increase in subject pulse rate can be set to cause the system to transmit a warning to a caregiver. However, an alert will not be generated when the pulse anomaly occurs during the time of day in which the subject exercises. Acting dynamically, the system discriminates between recurring exercise periods and isolated instances of strenuous activity.

The system can also monitor activities to detect temporal discrepancies in subject routine. For example, a subject who becomes violently ill might make several bathroom visits in a short time period. While the first visit violates no parameter boundary, the system detects the repetitive visits. Because of both the predetermined parameter settings and baseline data, the system detects a physical or behavioral irregularity-multiple trips to the rest room in an abnormally short period of time-and signals an appropriate party for investigation or other response.

A person skilled in the art will be able to practice the present invention in view of the present description, where numerous details have been set forth in order to provide a more thorough understanding of the invention. In other instances, wellknown features have not been described in detail in order not to obscure unnecessarily the invention, Having described and illustrated the principles of the invention in various embodiments thereof, it should be apparent that the invention can be modified in arrangement and detail without departing from such principles. I therefore claim all modifications and variations coming within the spirit and scope of the following claims.

What is claimed is:

1. A system for monitoring health parameters of a plurality of ambulatory subjects, comprising:
   a network, comprising:
      a computer;
      a remote node accessing the computer;
      a data storage device receiving and storing data acquired by the system; and
      a data analysis means in the computer for analyzing acquired data;
   a physiological monitoring subsystem coupled to the network, being operative to measure physiological parameters of the plurality of subjects and transmit parameter signals corresponding to measurements of the physiological parameters to the data storage device;

a behavioral and cognitive monitoring subsystem coupled to the network, being operative to measure behavioral and cognitive parameters of the plurality of subjects and transmit behavioral and cognitive signals corresponding to measurements of the behavioral and cognitive parameters to the data storage device; and a passive personal tracking subsystem coupled to the network, operative to generate tracking signals from tracking transmitters associated with each subject, said tracking signals corresponding to the identities and locations of each of the plurality of ambulatory subjects;

wherein the data analysis means is operative to associate the tracking signal of a first subject with a parameter signal of the first subject or a behavioral and cognitive signal of the first subject to form a data record.

2. The system of claim 1, wherein the physiological monitoring subsystem is operative to measure a physiological parameter of the subject irrespective of subject cooperation.

3. The system of claim 1, wherein the behavioral and cognitive monitoring subsystem is operative to measure a behavioral and cognitive parameter of the subject irrespective of subject cooperation.

4. The system of claim 1, the personal tracking subsystem further comprising a plurality of tracking sensors distributed throughout a facility having a defined multi-room space about which each of a plurality of subjects can freely move.

5. The system of claim 4, in which the presence, identity and movement of the subject are sensed by a proximate one of a plurality of subject tracking sensors distributed throughout the defined space, the proximate tracking sensor generating a corresponding tracking signal via the computer to the data storage device.

6. The system of claim 1, wherein the personal tracking subsystem generates a tracking signal irrespective of contemporaneous subject cooperation.

7. A system for monitoring a physiological parameter of a plurality of ambulatory subjects, comprising:

a plurality of personal tracking devices, each operative to produce a tracking signal corresponding to the identity and location of an ambulatory subject and transmit the tracking signal to a computer;

a plurality of tracking signal receivers distributed throughout a defined space structured to be occupied by any one of said subjects;

means for passively measuring a physiological parameter of any of the plurality of subjects, the means residing in an object or fixture in the defined area in which an ambulatory subject is present;

means for generating parameter signals corresponding to physiological parameter measurements;

means for transmitting parameter signals from the signal generating means to the computer;

means for creating data records by associating parameter signal of a subject with the tracking signal corresponding to that subject.

8. The system of claim 7, wherein the parameter measuring means functions irrespective of subject cooperation.

9. The system of claim 7, further comprising chronology identifying means for associating a chronological identifier with each parameter signal corresponding to a physiological parameter measurement.

10. A computer method for monitoring a health parameter of an ambulatory subject of a plurality of ambulatory subjects within a defined space, the method comprising:

measuring passively a health parameter of a subject by a first detector of a plurality of detectors positionable within the defined space, each detector of the plurality of detectors capable of detecting a health parameter of one subject of a plurality of subjects and generating a parameter signal corresponding to the measured parameter value;

transmitting the parameter signal to a network-coupled computer with a data storage device and a data analysis means;

associating the parameter signal with an identity by correlating a location of the first detector with subject identity and location, said subject identity and location determined by a spatial monitoring device producing subject signals corresponding to the identity and location of the subject;

creating a data record of the associated parameter signal with a subject identity determined by a spatial monitoring device producing signals corresponding to the identity and location of the subject; and storing the data record in a record uniquely associated with the subject.

11. A computer readable medium containing instructions adapted to cause a computer to perform the method of claim 10.

12. The method of claim 10, wherein storing the signal further comprises storing a chronological identifier in the record.

13. The method of claim 12, further comprising analyzing a plurality of stored signals in the record temporally to provide a trend for the monitored health parameter of the associated subject.

14. The method of claim 12, wherein analyzing a plurality of stored signals temporally further includes producing a histogram for each health parameter, using the stored signals and associated chronological identifiers, to indicate a trend.

15. The method of claim 10, further comprising:

providing a predetermined value range for a signal corresponding to the health parameter of the subject;

comparing the parameter signal of the data record to the predetermined value range; and generating an alert when the parameter signal corresponding to the measured health parameter is outside the predetermined value range.

16. The method of claim 10, further comprising:

providing a predetermined value range for signals corresponding to multiple health parameters of the subject;

comparing parameter signals of multiple data records to the respective predetermined value ranges; and generating an alert when each of the parameter signals corresponding to the measured health parameters are outside the predetermined value ranges.

17. A system for passively monitoring behavioral and cognitive health status of each of a plurality of ambulatory subjects, comprising:

a network-coupled computer with a data storage device and a data analysis means;

a spatial monitoring device, operative to produce subject signals corresponding to the identity and location of each of the ambulatory subjects and transmit the subject signals to the computer;

a passive medication compliance device, operative to produce a medication compliance signal corresponding to accessing a medication by each of the ambulatory subjects and transmit the medication compliance signals to the computer;

a first interactive physiological parameter measurement device, operative to produce parameter signals corresponding to measurements of physiological parameters of the subjects and transmit the parameter signals to the computer;

a sensor embedded in an article of regular and ordinary use by the subjects, operative to produce use signals corresponding to use of the article by subjects and transmit the use signals to the computer;

a nocturnal activity monitoring system, operative to produce nocturnal activity signals corresponding to restlessness of subjects and transmit the nocturnal activity signals to the computer; and data analysis means for analyzing signals produced by the above system components;

wherein the computer is operative to correlate a medication compliance signal, a parameter signal, a use signal, or a nocturnal activity signal with a specific subject based on the location of the device and the location of the subject derived from the subject signal.

18. The system of claim 17, the spatial monitoring device comprising:

a transmitter worn by the subject;

a plurality of receivers spatially distributed throughout the defined monitoring area; and signal generating means for generating a signal corresponding to a transmission received by a member of the plurality of spatially distributed receivers from the transmitter, the signal identifying and locating the subject.

19. The system of claim 18, wherein each of the plurality of receivers is uniquely identifiable by the data storage means.

20. The system of claim 18, wherein a plurality of said transmitters are worn by a plurality of said subjects, each transmitter transmits a subject identification code unique said subjects, so that each subject can be located by proximity to one of said receivers.

21. The system of claim 17, further comprising a chronological tagging means for tagging each signal with a chronological identifier.

22. The system of claim 17, further comprising environmental input logging means for logging changes input by the subject to a heating, ventilation and cooling system.

23. The system of claim 17, wherein the system monitors a plurality of subjects.

* * * * *